Nov. 10, 1959 W. H. HENDERSON Plant Pat. 1,878
CLEMATIS PLANT
Filed Oct. 10, 1958
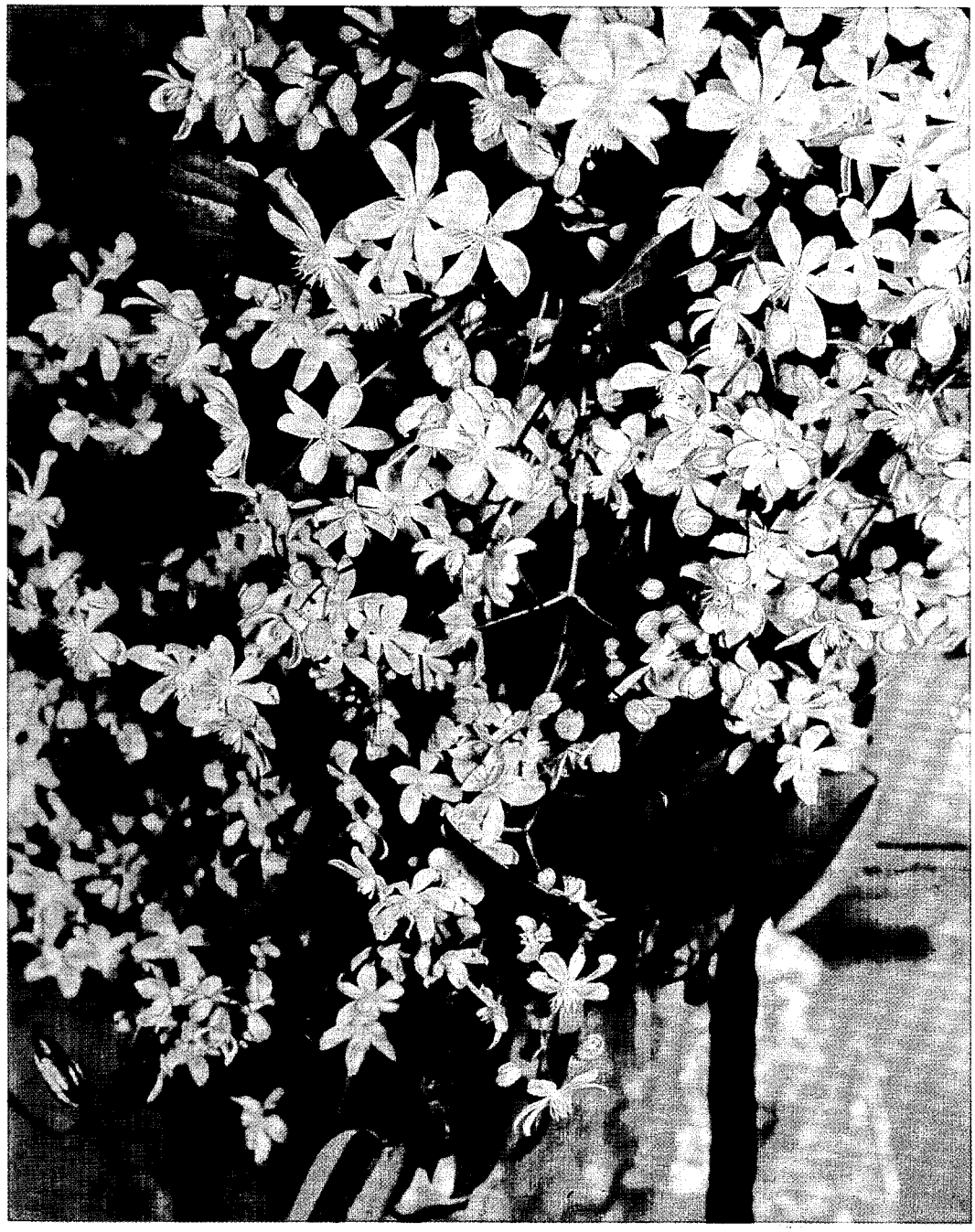
WILLIAM H. HENDERSON
INVENTOR
HUEBNER & WORREL
ATTORNEYS
BY Richard M. Worrel United States Patent Office Plant Pat. 1,878
Patented Nov. 10, 1959

1,878

CLEMATIS PLANT

William H. Henderson, Clovis, Calif.

Application October 10, 1958, Serial No. 766,638

1 Claim. (Cl. 47—60)

The present invention relates to a new and distinct variety of Clematis.

The subject plant is a new hybrid climbing evergreen Clematis and was hybridized by me at my experimental gardens at 2760 South Orange Avenue in Fresno, California. The parentage of the present plant is unnamed. For several years, I endeavored to cross pollinate different varieties of the *Clematis armandii* (unpatented) but was unable to do so or to get this species autogenously to produce seed. Eventually I obtained an Apple Blossom Clematis (unpatented) which had been imported from England. The Apple Blossom bears very pale pink to white blossoms having from eight to twelve petals as distinguished from the pure white four to six petal flowers characteristic of the *Clematis armandii*. I crossed the Apple Blossom with the *armandii* and suceeded in producing seeds. I subsequently planted these seeds and raised the first generation plants resulting from the cross pollination to florescence. Two of the unnamed first generation plants were selected by me, cross pollinated and produced seeds. These seeds in turn were planted and produced a second generation of hybrids. The instant variety of Clematis was selected from this second generation.

This new hybrid was carefully observed after its initial selection, cultivated by me, and subsequently asexually reproduced by me both by grafting and by rooting cuttings at my experimental gardens designated above and at my new experimental gardens at 4180 North Fowler Avenue, Fresno, California. The significant characteristics believed unique to the subject Clematis have consistently and successfully been reproduced in the asexual progeny of the present hybrid.

Novel characteristics of the hybrid Clematis disclosed herein are the intense pink coloration of its new growth, stems, and buds, its distinctive pink flowers, particularly the outer surfaces of the petals, and the large number of petals existing in the corollas of the flowers as compared with conventional Clematis. Further the stamen and pistils of the subject plant appear longer, and their respective androecium and gynoecium appear larger than normal. In addition, these clusters of stamens and pistils are more yellow, although not as chartreuse as the well-known *Clematis farquhariana* (unpatented) otherwise known as the Apple Blossom. In further comparison to the *Clematis farquhariana*, the subject Clematis grows more vigorously and to greater heights. Also, the leaves of the new hybrid are slightly more coarse and more leathery than the well-known parent *Clematis armandii*.

The accompanying drawing, reproduced from a color photograph, shows the subject plant including typical flowers and foliage. The photograph was taken shortly after the specimen of the plant was cut in the middle of March 1958.

The following is a more detailed description of the characteristics of the new Clematis with the color terminology employed being derived from the "Dictionary of Color" by Maerz and Paul, second edition.

Parentage: Unnamed hybrids selected from a succession of hybrids of *Clematis armandii* all crossed by the applicant.

Plant: A climbing evergreen with stem length and growth habits similar to the well-known *Clematis armandii*. The mature main stems and branches are Spanish Raisin, Plate 48–L–3 in color.

Leaves: The new or young leaves are predominantly the color of Plate 8–H–1 on their ventral surfaces though tinged with a green blush which is prominent at their tips. The dorsal surfaces of the young leaves have the color of Plate 14–B–4, Antelope Dust +, with a slight red blush.

The leaves in an intermediate stage of growth are approximately the color of Plate 8–J–12 and have a blade width of approximately three-fourths of an inch, generally lanceolate, a slightly undulated margin, and are similar in other respects to the mature leaves, as described below.

The blades of the mature leaves are approximately one inch in width and approximately two and seven-eighths inches in length, oblong, palmately net-veined, acuminate, marginally entire, and with their bases rounded; the dorsal surface color is Plate 21–J–1, Grape Green, while the ventral surface color is Plate 22–K–4; the petioles of the mature leaves are short, generally cylindrical, and are identified in color by Plate 16–C–11.

Flowers: The new petals in the closed pods have the color of Plate 46–I–1 to Plate 50–E–2 on their dorsal surface. When the pods open fully exposing the mature petals, the ventral surfaces appear in color like Plate 50–E–2 while the dorsal surfaces are more nearly similar in color to Plate 50–B–1. The mature petals are approximately five-sixteenths of an inch in width and approximately five-eighths of an inch in length, are elliptical, and marginally entire. The flowers of the subject Clematis possess a high degree of fragrance and bloom during the normal blooming periods of the parent *Clematis armandii*. There are from four to six to six petals in each corolla with a very high percentage having five petals. The pistils have a color of Plate 9–L–1 while the pedicels are Plate 46–K–1 for both open and closed petals.

Having thus described my new Clematis, I claim:

A new and distinct variety of Clematis plant characterized by the pink color of its new growth and flowers and by the large number of petals in each corolla.

No references cited.